(12) United States Patent
Canales Espinosa de los Monteros et al.

(10) Patent No.: US 10,251,794 B2
(45) Date of Patent: Apr. 9, 2019

(54) BAG FOR PACKING DISPOSABLE HYGIENE ITEMS

(71) Applicant: Grupo P.I. Mabe, S.A. de C.V., Puebla (MX)

(72) Inventors: Carlos Canales Espinosa de los Monteros, Puebla (MX); Lucia del Carmen Sanchez Fernandez, Puebla (MX)

(73) Assignee: GRUPO P.I. MABE, S.A. DE C.V., Puebla (MX)

( * ) Notice: Subject to any disclaimer, the term of this patent is extended or adjusted under 35 U.S.C. 154(b) by 0 days.

(21) Appl. No.: 15/501,600

(22) PCT Filed: Aug. 4, 2014

(86) PCT No.: PCT/IB2014/063690
§ 371 (c)(1),
(2) Date: May 12, 2017

(87) PCT Pub. No.: WO2016/020720
PCT Pub. Date: Feb. 11, 2016

(65) Prior Publication Data
US 2017/0246057 A1    Aug. 31, 2017

(51) Int. Cl.
*A61F 13/551*    (2006.01)
*B65D 33/25*    (2006.01)
*B65D 33/10*    (2006.01)

(52) U.S. Cl.
CPC .... *A61F 13/55145* (2013.01); *A61F 13/5511* (2013.01); *B65D 33/10* (2013.01); *B65D 33/25* (2013.01)

(58) Field of Classification Search
CPC .......... A61F 13/55145; A61F 13/5511; B65D 33/10; B65D 33/25
(Continued)

(56) References Cited

U.S. PATENT DOCUMENTS 2,750,033 A * 6/1956 Pickens ............. A61F 13/55145
206/361
2,991,001 A * 7/1961 Hughes .................. B65D 33/20
383/210.1
(Continued)

FOREIGN PATENT DOCUMENTS

ES    2410980 T3    7/2013
MX    195354    2/2000
(Continued)

OTHER PUBLICATIONS

International Preliminary Report on Patentability; PCT/IB2014/063690; filed Aug. 4, 2014.
(Continued)

*Primary Examiner* — Ernesto A Grano
(74) *Attorney, Agent, or Firm* — Vivicar Law, PLLC

(57) ABSTRACT

The present invention refers to a flexible packaging, comprised by a polyethylene film, which is useful for packing disposable absorbent articles, such as disposable diapers and panties for babies and adults, feminine pads, pantiliners and the like, which may be opened and closed as many times as needed, wherein it comprises a closing system that is not altered nor loses functionality during the use and allows to open the bag to remove an article and close it again so as to protect the articles that remain inside the bag and avoid the dust, bugs or particles that may pollute same.

8 Claims, 2 Drawing Sheets

(58) Field of Classification Search
USPC ................................................. 206/570
See application file for complete search history.

(56) References Cited

U.S. PATENT DOCUMENTS

| | | | |
|---|---|---|---|
| 3,780,781 A | 12/1973 | Uramoto | |
| 3,827,472 A | 8/1974 | Uramoto | |
| 3,982,687 A | 9/1976 | Auer et al. | |
| 3,990,627 A * | 11/1976 | Olson | B65D 33/20 383/62 |
| 4,410,130 A * | 10/1983 | Herrington | B65D 33/20 383/211 |
| 4,539,705 A | 9/1985 | Baines | |
| 4,955,981 A | 9/1990 | Provost | |
| 5,024,537 A | 6/1991 | Tilman | |
| 5,026,563 A | 6/1991 | Erden et al. | |
| 5,063,069 A | 11/1991 | Erden et al. | |
| 5,172,980 A | 12/1992 | Provost | |
| 5,205,649 A * | 4/1993 | Fullerton | B65D 33/1691 383/108 |
| 5,476,323 A * | 12/1995 | Gold | B65D 33/18 229/80.5 |
| 5,885,262 A * | 3/1999 | Wheeler | B65D 31/02 156/580.1 |
| 5,908,243 A * | 6/1999 | Hanning | B65D 33/18 383/5 |
| 6,012,844 A * | 1/2000 | Huseman | B65D 33/20 383/209 |
| 6,196,716 B1 * | 3/2001 | Geyer | B65D 33/34 383/42 |
| 6,345,911 B1 | 2/2002 | Young et al. | |
| 6,461,044 B1 * | 10/2002 | Anderson | B65D 33/20 383/204 |
| 6,601,706 B2 | 8/2003 | McManus et al. | |
| 6,607,170 B1 * | 8/2003 | Hoftman | A61B 50/37 206/370 |
| 7,424,796 B2 * | 9/2008 | Shepard | B65B 61/188 53/133.4 |
| 7,585,111 B2 | 9/2009 | Turvey et al. | |
| 8,800,250 B2 * | 8/2014 | Moehlenbrock | B65D 33/20 493/212 |
| 9,610,128 B2 * | 4/2017 | Hartley | A61B 50/39 |
| 9,919,844 B2 * | 3/2018 | Taylor | B65D 33/14 |
| 2002/0104774 A1 * | 8/2002 | Hammond | A61F 17/00 206/570 |
| 2003/0169947 A1 | 9/2003 | Taheri | |
| 2004/0178099 A1 * | 9/2004 | Natay-Curley | A61L 2/07 206/370 |
| 2006/0062496 A1 * | 3/2006 | Clune | A44B 18/0084 383/95 |
| 2008/0152264 A1 * | 6/2008 | Pokusa | B65B 9/067 383/5 |
| 2008/0182739 A1 * | 7/2008 | Madson | B65D 33/25 493/214 |
| 2009/0266036 A1 * | 10/2009 | Zerfas | B65B 9/042 53/469 |
| 2009/0279813 A1 * | 11/2009 | Pokusa | B65D 33/20 383/211 |
| 2010/0078351 A1 * | 4/2010 | Sherrill | A61F 13/551 206/570 |
| 2011/0036741 A1 * | 2/2011 | Moehlenbrock | B65B 9/067 206/484 |
| 2011/0038570 A1 * | 2/2011 | Moehlenbrock | B65B 9/067 383/211 |
| 2011/0038571 A1 * | 2/2011 | Moehlenbrock | B65B 9/067 383/211 |
| 2011/0062051 A1 * | 3/2011 | Miller | B65D 75/008 206/570 |
| 2011/0103718 A1 * | 5/2011 | Bosman | B65D 75/008 383/66 |
| 2011/0147383 A1 * | 6/2011 | Soudais | B32B 27/32 220/270 |
| 2012/0292224 A1 * | 11/2012 | Matsushima | B65D 33/01 206/525 |
| 2013/0126388 A1 * | 5/2013 | Hannahan | A61F 13/55145 206/570 |

FOREIGN PATENT DOCUMENTS

| | | |
|---|---|---|
| MX | 230104 | 7/2005 |
| MX | 257432 | 5/2008 |
| MX | 2010004522 A | 10/2010 |
| WO | 2003104087 A2 | 12/2003 |
| WO | 2013122972 A1 | 8/2013 |
| WO | 2016020720 A1 | 2/2016 |

OTHER PUBLICATIONS

International Search Report; PCT/IB2014/063690; Filed Aug. 4, 2014.
International Search Report—English Translation; PCT/IB2014/063690; Filed Aug. 4, 2014.
Written Opinion of the International Searching Authority; PCT/IB2014/063690; Filed Aug. 4, 2014.
Written Opinion of the International Searching Authority—English Translation; PCT/IB2014/063690; Filed Aug. 4, 2014.
European Search Opinion in corresponding European App. No. 14 899 200.1, dated Feb. 9, 2018.

* cited by examiner

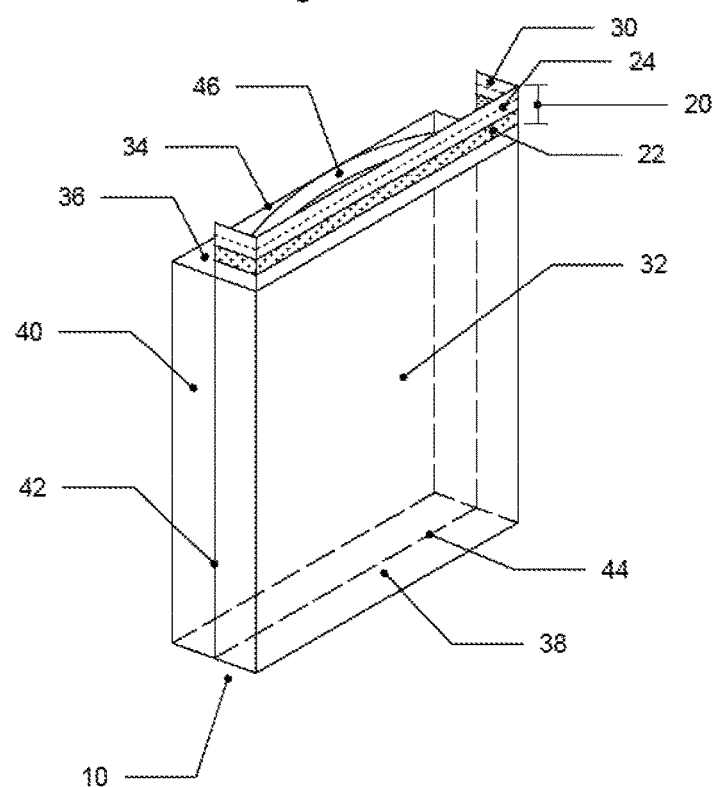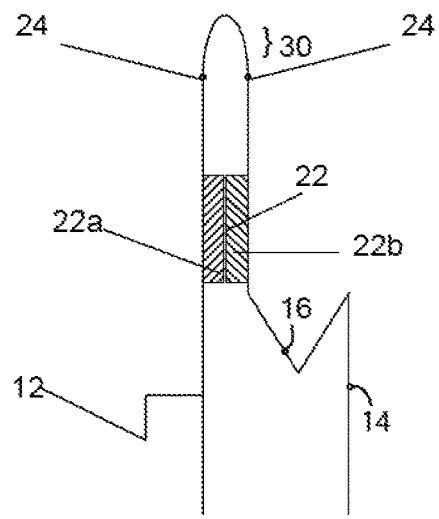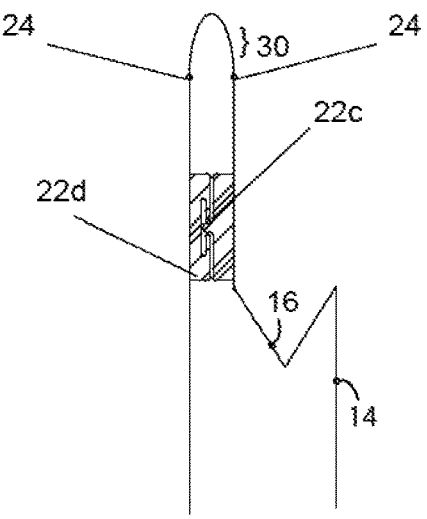

BAG FOR PACKING DISPOSABLE HYGIENE ITEMS

TECHNICAL FIELD OF THE INVENTION

The present invention refers to disposable hygienic articles packaging having the particularity of being semi-tight closeable by means of a device that protects the item that remains inside the packaging. More particularly, the present invention refers to hygienic articles packaging which comprise a closing system and an easy-opening system.

BACKGROUNDS OF THE INVENTION

The disposable hygienic articles are articles used to absorb and contain bodily exudates, among them there are disposable diapers and underwear for infants, disposable diapers, panties and towels for adults, feminine pads, pantiliners, etc.

Traditionally, these items are packaged in flexible, usually polyethylene packaging, containing several articles placed one next to the other in compressed form in order to optimize the packaging and the shelf space. Said packagings usually have an "easy-opening" system consisting in one or several weakening lines whereby the packaging can be easily opened to get the product out. This kind of products are used one at a time, i.e., one is taken out and while it is used, the rest of the articles remain inside the bag. The approximate time of use of each of the articles ranges from 3 to 12 hours (when are used by night); in this way, if the packaging contains 10 articles, once this was opened to get the first article out, the rest of the articles may remain within the opened package for more than 3 days. This, in the best of the cases, as there are packagings that contain up to 100 or more pieces, implying that the last article will be used from 20 to 30 days after the package was opened, being exposed to pollution by dust, bugs, etc. Thus, it is very convenient to pack this type of articles in flexible packaging having the possibility that, once opened, they may be closed again such that the articles are protected from pollution, dust, etc.

Some attempts have been made to achieve this objective; such is the case of the U.S. Pat. No. 3,982,687 of Kimberly Clark, which describes a flexible bag which, through the top front or rear portion, is fitted with a strap attached by the side seals. This strap is used in order to close the bag once it was opened, which is inserted into a hole placed above the strap by the front and rear portions of the bag, such that, besides closing the bag, the strap forms a handle for the transportation thereof. While the bag may be opened and sealed as many times as necessary by this strap, same does not provide a tight closing that prevents pollution from entering into the bag, besides the fact that the use of this type of closing is complex for a user.

U.S. Pat. No. 6,601,706, also of Kimberly Clark, describes a bag for the packaging of absorbent disposable articles which, in its top portion, has a fin that extends from one of the front or rear faces of the bag, this fin is bent towards the opposing face for closing the bag; the fin further has adhesive that helps the fin to adhere to this opposing face so the bag may remain closed. The adhesive has suitable characteristics in such a way that it allows for the bag to be opened and closed as required, however, this system does not provide a tight closing, besides the adhesive can easily become polluted and hinder the good operation of the bag; furthermore, when the adhesive becomes polluted, it ceases to have its closing properties.

On the other hand, Mexican patents MX 195354, MX 230104 and MX 257432, all to Grupo P. I. Mabe, describe a bag with a tab or closing tab, in such a way that once the disposable absorbent articles are introduced into the bag, the tab is turned so as to close same. The bag may be opened and closed through the tab as many times as needed. Similarly to the previous packagings, this closing tab does not provide means for tightly closing the bag, in such a way to avoid any kind of pollution.

There exist a myriad of proposals of resealable bags, mainly containing a closing system commercially known as "zip lock" which consists of two elements that are attached separately to each of the opposing faces of a bag and placed facing each other, usually at the top of the bag; these elements are coupled with a male-female type system closing the bag tightly. On the other hand, the use of a system with hooks and loops (commercially known as "velcro" type, a registered trademark of Velcro Industries) is also known in the market for bags of flexible materials, such that they may be opened and closed when necessary.

Examples of these systems a described in U.S. Pat. Nos. 4,955,981, 5,026,563, 5,024,537, 5,063,069, 5,172,980, 7,585,111, which are mainly addressed to food packaging packaging and describe different forms of placing this kind of systems.

The use of this type of systems for packaging disposable absorbent articles is not described in any case, this, considering the difficulty represented by the fact that the packaging for these items requires side or top and bottom bellows to achieve the suitable accommodation of the articles inside the bag; that are articles manufactured in high speed production lines (up to 700 articles/minute) and that it is very convenient for the packaging to have a handle for the transportation thereof.

The present invention covers a flexible packaging for packing disposable hygienic articles that provides the possibility of semi-tightly closing it, once it is opened for the first time, as many times as needed. Each time an article is taken out from the packaging, this may be semi-tightly closed again by means of a tight-seal type closing (zip-lock) or a hooks and loops type closing, such that the product that remains within the packaging is not polluted; in addition, the packaging has an easy-opening system that allows for it to be opened by means of this system without the need of breaking or tearing the same and without affecting the closing system. The packaging may further have a handle for its comfortable transportation.

OBJECTIVES OF THE INVENTION

The objective of the present invention is to provide the consumer with a flexible packaging for disposable absorbent articles that, once opened, it may be semi-tightly closed again by means of a device that protects the product that remains within the packaging from dust, bugs, etc.

An additional objective of the invention is that said packaging has also an easy-opening type opening.

A further objective of the invention is that the flexible packaging has the design suitable so as to be used for packing products that are manufactured in a high speed continuous manufacturing line.

Another objective of the invention addresses for the packaging to have a handle for the transportation thereof.

BRIEF DESCRIPTION OF THE DRAWINGS

FIG. 3 is an isometric view of the bag of the invention filled with product.

FIG. 4 illustrates a cut through line A-A" of FIG. 2.

FIG. 5 shows an alternative of the closing system of the bag of the invention.

DETAILED DESCRIPTION OF THE INVENTION

The present invention refers to a flexible packaging, usually comprised by a polyethylene film for packing disposable absorbent articles, such as disposable diapers and panties for babies and adults, feminine pads and pantiliners and the like, which may be opened and closed as many times as needed by means of a closing system that is not altered, nor loses functionality during the use and allows to open the bag to remove an article and close it again in an easy and safe way. The opening system used in the flexible packaging of the invention is a semi-hermetic system that protects the articles that remain inside the bag from dust, bugs or particles that may pollute same.

Figure 1:
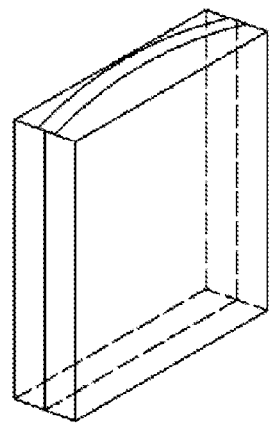
FIG. 1 shows a flexible bag of the prior art for the packaging of disposable absorbent articles.

The disposable absorbent articles are manufactured in production lines at a speed of between 300 and 700 articles per minute and are packed in compact groups, of 10, 20, 30, 50, or the number of articles required. Thus, the packaging design must be such that it allows for the fast and effective packing of the articles when it leaves the production line. Flexible bags with a top bellow and side seals are generally used, such that the articles are introduced at the bottom of the bag to then seal it so that it acquires a polyhedron arrangement such as that shown in FIG. 1, which shows a bag of the prior art. The bags can have a handle at the top for ease of transportation and an easy-opening system that allows to open the bag without tearing or deforming the film from which same is made.

Figure 2:
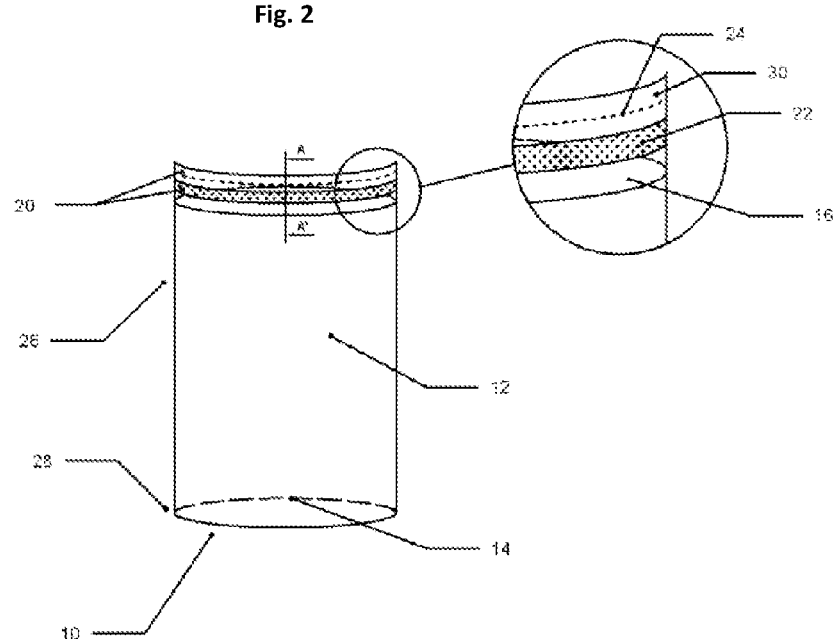
FIG. 2 shows the bag of the invention before the product is introduced therein.

FIG. 2 shows the flexible packaging (10) of the present invention before introducing the articles inside same; it has a top part (26) and a bottom part (28) and is comprised by a front face (12), a rear face (14), a top face or bellows (16) and the opening system (20) of the present invention placed over the top thereof. In the fig re, the packaging (10) is shown opened by the bottom part (28), such that through this bottom part (28) the disposable absorbent articles that will be contained within same are introduced, once the articles inside, the packaging takes a rectangular polyhedron form; it is subsequently sealed by means of the sealing line (44) shown in FIG. 3, thus forming the bottom face of the packaging (10).

As shown in FIG. 2, the opening system (20) of the flexible packaging (10) of the present invention is comprised by a closing system (22) and an easy-opening system; both systems are placed over the top of the packaging along the front (12) or rear (14) face.

The closing system (22) allows for the bag to be semi-tightly opened and closed, such that the product is protected from pollution, dust and bugs. The easy-opening system is comprised by a weakening line (24) and a removable strip (30) that is placed above the weakening line (24); in order to open the packaging, the strip (30) is detached, however, once the removable strip (30) is removed, the flexible packaging remains closed by means of the closing system (22); in order to have access to the product, it is necessary to open the closing system (22). This closing system (22) can be anyone that allows to semi-tightly open and close the packaging, such as a hooks and loops type system, a "zip lock" type system, a zipper type system, etc., such that once the packaging (10) is opened to remove the required article or articles, this can be closed, protecting the product that remains within same from dust, bugs and general pollution.

Once the articles are introduced within the packaging, this takes the form of a rectangular polyhedron, such as the one shown in FIG. 3, with a front view (32), a rear view (34), two side views (40), a top view (36) and a bottom view (38). The Figure also shows the opening system (20) of the packaging (10) of the present invention, which is comprised by an easy-opening system and a closing system (22). In order for the packaging to be used for disposable absorbent articles, the opening system (20) must be placed entirely in the front view (32) (embodiment shown in FIGS. 2 and 3) or in the rear view (34), also encompassing a portion of the side views (40) as shown in FIG. 3. In this way, the upper bellows (16) that, when the packaging is filled with product, conforms the top face (36) thereof is completely flat and the opening system does not interfere with this top face, such that the appearance of the packaging is not lost, which is important for the transportation, storage and display of the products, likewise, it is important in order for the packaging to acquire the rectangular polyhedron arrangement shown in FIG. 3 and for the placement of the handle (46).

It should be noted that the side views (40), are comprised on one hand by the front face (12), a portion of the rear face (14) and by the side seals (42).

FIG. 4 shows a cut through line A-A' of FIG. 2, the opening system (20) of the flexible packaging of the present invention may be seen, which contains the easy-opening system and the closing system.

In order to conform this opening system, the flexible film from which the packaging is comprised, extends upwards, through the top part (26), either by the front face (12) or by the rear face (14) and turns on itself, forming an inversed "U". The easy-opening system and the closing system (22) are placed within this inversed "U" as shown in FIG. 4. At the bottom part of the inversed "U", the closing system (22) is attached, which is comprised by two elements: a first element (22a) and a second element (22b), each of which is attached to one of the faces of the "U" at the inner portion thereof. This closing system may be a hook and loop type system, a zip lock type system, a zipper type system or any other system known in between that is comprised by two elements that, when being attached, achieve a tight or semi-tight closing. Each of the first and second elements have a flat face by which same are attached to the flexible film that comprises the packaging and, by the opposing face, they have the cited closing system.

In the case of a velcro type system (such as that shown in FIG. 4), the first element, on the face opposing the flat face, has hooks and the second element has loops, so when both elements are attached, the hooks are connected in the loops thus forming the closing system (22) of the present invention. This closing system (22) is attached to the flexible film by means of adhesive, by sealing or by heating, or any other known means.

The easy-opening system that is part of the opening system (20) of the packaging, consists of a swage or weakening line (24) and a removable strip (30). The swage (24) is placed along all the width of the front part (12) of the packaging, above the closing system (22) and is conformed in both layers of the inversed "U", as shown in FIGS. 2 to 5. The removable Strip (30) is the part of the flexible film that is placed above the weakening line or swage (24), precisely where the flexible film goes back on itself to form the inversed U, by the top part thereof, so that same contains part of both faces of the inversed U.

The packaging (10) may further have a handle (46) for its easy transportation, as shown in FIG. 3. The handle (46) is usually a strip of the same flexible film of the packaging, which is attached thereto adjacently to the side seals (42), by the top part thereof. This strip has a maximum width equal to the top view width (36) of the packaging and a minimum length equal to the width of the front (12) or rear (16) faces.

FIG. 5 shows an alternative to the closing system (22) consisting of an airtight-seal type system (zip-lock). In the same way as the velcro type closing system, the airtight-seal type closing system (zip-lock) is comprised by a first element (22c) and a second element (22d), each one of which has a flat face affixed to the inner portion of the inversed "U", by the bottom part thereof, and a non-flat face with the appropriate form of the elements of an airtight-seal type system "zip lock" (male and female) that when being attached, comprise an alternative for the semi-tight closing system of the packaging (10) of the present invention, which can be opened and closed as many times as needed without damaging or altering the packaging material, protecting the articles that remain within the same from pollution with dust or bugs. There are many arrangements known in the market for the male-female system of an airtight-seal type system (zip-lock), any of which may be used in the packaging of the present invention.

To ensure that the bag will remain closed and the closing system will not open with the normal handling thereof, same must have a minimum peel-strength, measured at 180°, of 150 g/cm. This strength is calculated using the following test method:

Three 2.54 cm (1 inch) width cuts are made to an empty bag, and with a length that spans from the top part of the opening system (top part of the inversed "U"), to 2.54 cm (1 inch) below the closing system:
At the right end (sample 1)
At the left end (sample 2)
At the middle (sample 3)
The strip (30) is removed from the easy-opening system to each of these samples;
The samples are held in the clamps of the dynamometer placing one of the faces of the "U" in the top clamp and the opposing face of the "U" in the bottom clamp (simulating the stress applied when opening the closing system);
The dynamometer is actuated to a 30.48 cm/min speed. (12 inch/min);
Data are recorded at the time of opening the closing system and is informed in g/cm (g/inch).

While the invention has been described based on a currently preferred embodiment, it is clear that various changes and modifications thereof can be made, such changes and modifications being within the spirit and scope of the invention, as defined in the attached claims.

The invention claimed is:

1. A flexible packaging for disposable absorbent articles composed of a polyethylene film which can be opened and closed semi-tightly, comprising
a front face (12),
a rear face (14),
a top bellows (16),
a top part (26),
a bottom part (28), and
an opening system (20), wherein
the top part (26) has a distal end located above the top bellows (16);
the front face (12) has a width and first longitudinal edges, the rear face (14) has a width and second longitudinal edges, and wherein the first longitudinal edges are sealed to the second longitudinal edges by a first side seal and a second side seal (42);
the flexible packaging (10) in both an open and closed state has in the distal end of the top part (26) an inverted U-shape member, which is an extension of the front face (12) and is located above the top bellows (16), comprising an upward layer and a downward layer, such that the upward layer extends upwards continuous with the front face (12), above the top bellows (16) of the flexible packaging (10) and subsequently turns downwardly onto itself, thereby forming the downward layer, wherein the downward layer reaches the top bellows (16) of the flexible packaging (10) adjacent to the front face (12) of the flexible packaging (10) and is folded in a V-shape, thereby forming the top bellows (16) of the flexible packaging (10);
and wherein the opening system (20) is located within the inverted U-shape member.

2. The flexible packaging for disposable absorbent articles as claimed in claim 1, wherein the opening system (20) comprises a closing system (22) and an easy-opening system; such that the easy-opening system is located upwards of the closing system (22), and wherein the closing system (22) has a peel-strength.

3. The flexible packaging for disposable absorbent articles as claimed in claim 2, wherein the closing system (22) comprises a first element and a second element;
the first element is bonded to the upward layer and the second element is bonded to the downward layer;
the first element faces the second element and the second element faces the first element, such that the first element and the second element together are capable of closing the flexible packaging semi-tightly.

4. The flexible packaging for disposable absorbent articles as claimed in claim 3, wherein the closing system (22) is a hook and loop type system.

5. The flexible packaging for disposable absorbent articles as claimed in claim 3, wherein the closing system (22) is an airtight-seal type system (zip lock).

6. The flexible packaging for disposable absorbent articles as claimed in claim 2, wherein the easy-opening system comprises a weakening line (24) and a removable strip (30), such that the weakening line (24) comprises all the width of the front face of the flexible packaging;
the removable strip (30) is placed above the weakening line (24); and
the easy-opening system, the closing system, the weakening line and the removable ship are located in both the upward layer and the downward layer of the inverted U-shape.

7. The flexible packaging for disposable absorbent articles as claimed in claim 2, wherein the peel-strength of the closing system (22), measured at 180°, is at least 150 g/cm.

8. The flexible packaging for disposable absorbent articles as claimed in claim 1, wherein the flexible packaging (10) further comprises a handle (46) comprising a strip of the same polyethylene film from which the packaging is composed, wherein the handle (46) is adjacently attached to a first top part of the first side seal and a second top part of the second side seal (42), such that the handle (46) has a maximum width equal to a width of the top bellows of the flexible packaging when the flexible packaging is filled with disposable absorbent articles, and a minimum length equal to the width of the front face (12) or the width of the rear face (14).

* * * * *